United States Patent [19]

Hsu et al.

[11] Patent Number: 5,194,167

[45] Date of Patent: Mar. 16, 1993

[54] QUATERNARY AMMONIUM SALTS OF MERCAPTOTHIADIAZOLES AND RELATED HETEROCYCLIC DERIVATIVES AS ANTIOXIDANT AND ANTIWEAR ADDITIVES

[75] Inventors: Shih-Ying Hsu, Morrisville, Pa.; Andrew G. Horodysky, Cherry Hill, N.J.

[73] Assignee: Mobil Oil Corporation, Fairfax, Va.

[21] Appl. No.: 697,039

[22] Filed: May 8, 1991

[51] Int. Cl.$^5$ .......................................... C10M 133/38
[52] U.S. Cl. ............................... 252/34; 252/47.5; 252/402; 548/127; 548/128; 548/129; 548/130; 548/134; 548/135; 548/136
[58] Field of Search ............. 252/34, 47.5, 402; 548/127, 128, 129, 130, 134, 135, 136

[56] References Cited

U.S. PATENT DOCUMENTS

| | | | |
|---|---|---|---|
| 3,897,351 | 7/1975 | Davis et al. | 252/34 |
| 4,283,296 | 8/1981 | Nebzydoski et al. | 252/34 |
| 4,741,847 | 5/1988 | Cargnino et al. | 252/47.5 |
| 4,764,298 | 8/1988 | Croudace | 252/47.5 |
| 4,917,809 | 4/1990 | Zinke et al. | 252/34 |
| 5,073,279 | 12/1991 | Farng et al. | 252/47.5 |

*Primary Examiner*—Jacqueline Howard
*Attorney, Agent, or Firm*—Alexander J. McKillop; Charles J. Speciale; Howard M. Flournoy

[57] ABSTRACT

Quaternary ammonium salts of mercaptothiadiazoles and related heterocyclic derivatives have been found to be effective antioxidant and antiwear additives for lubricants and fuels.

23 Claims, No Drawings 5,194,167

QUATERNARY AMMONIUM SALTS OF MERCAPTOTHIADIAZOLES AND RELATED HETEROCYCLIC DERIVATIVES AS ANTIOXIDANT AND ANTIWEAR ADDITIVES

BACKGROUND OF THE INVENTION

1. Field of the Invention

This application is directed to quaternary ammonium salts of mercaptothiadiazoles and related heterocyclic derivatives as multifunctional antioxidant/antiwear additives for lubricants and fuels and to compositions containing same.

Lubricants, such as lubricating oils and greases, are subject to oxidative deterioration at elevated temperatures or upon prolonged exposure to the elements. Such deterioration is evidenced, in many instances, by an increase in acidity and in viscosity, and when the deterioration is severe enough, it can cause metal parts to corrode. Additionally, severe oxidation leads to a loss of lubrication properties, and in especially severe cases this may cause complete breakdown of the device being lubricated. Many additives have been tried, however, many of them are only marginally effective except at high concentrations. Improved antioxidants are clearly needed.

Antioxidants or oxidation inhibitors are used to minimize the effect of oil deterioration that occur when hot oil is contacted with air. The degree and rate of oxidation will depend on temperature, air and oil flow rates and, of particular importance, on the presence of metals that may catalytically promote oxidation. Antioxidants generally function by prevention of peroxide chain reaction and/or metal catalyst deactivation. They prevent the formation of acid sludges, darkening of the oil and increases in viscosity due to the formation of polymeric materials.

Additionally, lubricants are under heavy stress that can affect their extreme pressure/antiwear and load carrying ability particularly between steel on steel moving surfaces.

2. Description of Related Art

The use of thiadiazole derivatives, such as 2,5-dimercapto-1,2,4-thiadiazole, for their antioxidant, anticorrosion and metal passivating properties when incorporated into oleaginous compositions is well known as disclosed in U.S. Pat. No. 4,661,273, U.S. Pat. No. 4,678,592 and U.S. Pat. No. 4,584,114. U.S. Pat. No. 4,410,703 discloses the use of thiadiazoles substituted with certain other moieties such as the organophosphorous moiety.

It is an object of this invention to provide lubricant compositions having enhanced oxidative stability, reduced wear, increased load carrying/EP capabilities and improved lubricity. Additional benefits can include antifatigue, cleanliness, detergency, dispersal, corrosion inhibiting, antirust antispilling, friction reducing, low-temperature improving and combustion improving properties. It also is an object of this invention to provide improved fuel compositions.

Traditional quaternary ammonium salts consist of a) a tetra-alkylated amine cation, and b) an inorganic counter-anion such as halide, perchlorate and hexaflurophosphate, etc. These quaternary salts have been widely used in industrial and household applications as cleaning detergents. Little or no attention has been paid to them for use as lubricant additives due to their ionic nature which can make them incompatible with and insoluble in organic lubricating oils. However, these difficulties have been addressed by our recent finding that selected quaternary ammonium salts can be converted into organic quaternary ammonium salts composed of a (alkyl)x(aryl)yN+, where x+y=4, cation and an organic counteranion such as anionic dimercaptothiadiazole as exemplified in this patent. These organic quaternary ammonium salts are generally soluble in both mineral base stocks and ester-based synthetic lubricants and exhibit surprisingly good antioxidant and antiwear activities.

SUMMARY OF THE INVENTION

This invention is directed to novel quaternary ammonium salts of mercaptothiadiazoles and related heterocyclic derivatives as multifunctional antioxidant and antiwear additives and to their use in lubricant and fuel compositions to improve their performance properties.

These classes of compounds disclosed in this patent application are different from those prior art ionic compounds containing acidic protons such as a mixture of carboxylic acids and amines; these are not desirable in lubricant compositions because they may act as pro-oxidants or oxidation accelerators. The organic quaternary ammonium salts disclosed herein contain no undesirable acidic protons and, to the best of our knowledge, have not been synthesized and manufactured elsewhere. Their syntheses and applications as antioxidant and antiwear additives in lubricating compositions are therefore novel. Similar benefits are expected with the use of these novel additives in hydrocarbon, oxygenated and/or mixed fuel formulations such as gasoline or gasohol.

DESCRIPTION OF PREFERRED EMBODIMENTS

Generally speaking the mercaptothiadiazole or related heterocyclic is reacted with a quaternary ammonium halide in the presence of an alkanol and an alkali metal hydroxide, the resultant intermediate product is then reacted with a hydrocarbyl acid anhydride to afford the final desired product.

The organic ammonium salt antioxidants described can be easily prepared at ambient temperature in almost quantitative yields as exemplified in FIGS. 1, 2 and 3. 2,5-Dimercapto 1,3,4-thiadiazole is used only for illustration purposes; other hetercycles such as 2-mercaptobenzothiazole (Example 1) can also be employed where only one mercaptan group is involved for functionalization. The quaternary ammonium salts illustrated here can be other types of organic cations such as N-alkyl pyridinium halide, sulfonium salts, or triphenylmethyl salts, etc. These salts of organic cation can exist in either unalkylated form or in alkylated/polymer-supported form.

Possible products are shown below. Other related products are possible.

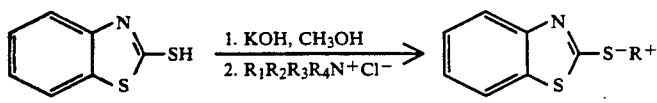

(Figure 1)

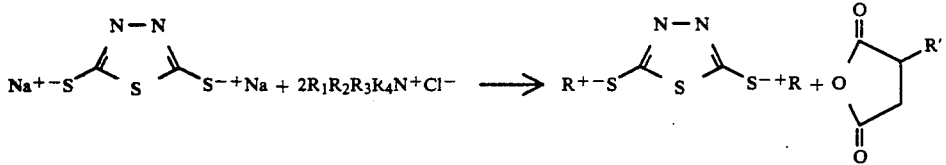

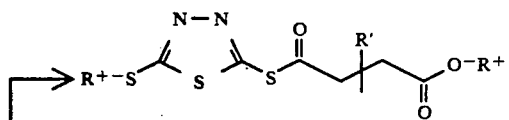

(Figure 2)

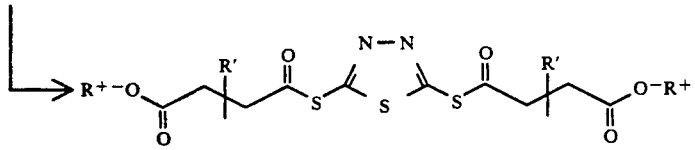

(Figure 3)

Where $R^+ = N^+R_1R_2R_3R_4$, a tetra-substituted ammonium ion, the substituted group attached to nitrogen can be the same or different; and can be $C_1$ to about $C_{40}$ hydrocarbyl, preferably $C_1$–$C_{18}$, or aryl and can optionally contain sulfur, nitrogen and/or oxygen; $R' = C_1$ to about $C_{40}$ hydrocarbyl, such as alkyl or alkenyl or a polyhydrocarbyl such as polyisobutenyl, or polypropenyl.

The quaternary ammonium salts disclosed are made from mercapto-heterocyclic compounds wherein all or essentially all of the one, two, or three or more available mercapto groups have been converted to form the described salt derivatives.

Suitable thiadiazoles include any appropriate mercapto-thiadiazole, however, preferred is 2,5-dimercapto-1,3,4-thiadiazole. Some suitable examples include but are not limited to 3,4-dimercapto-1,2,5-thiadiazole, 3,5-dimercapto-1,2,4-thiadiazole, 4,5-dimercapto,1,2,5-thiadiazole, 4,5-dimercaptobenzo 1,2,3-thiadiazole, 4,7-dimercaptobenzo 1,2,3-thiadiazole, 4,6-dimercaptobenzo 1,2,3-thiadiazole, 5,6-dimercaptobenzo 1,2,3-thiadiazole, 5,7-dimercaptobenzo 1,2,3-thiadiazole, 6,7-dimercaptobenzo 1,2,3-thiadiazole, 4,5-dimercaptobenzo 2,1,3-thiadiazole, 4,6-dimercaptobenzo 2,1,3-thiadiazole, 5,6-dimercaptobenzo 2,1,3-thiadiazole, 5,7-dimercaptobenzo 2,1,3-thiadiazole, 6,7-dimercaptobenzo 2,1,3-thiadiazole.

The organic cations as noted above are not limited to quaternary ammonium salts but can include other organic cations as noted hereinabove.

Conditions for the above reactions may vary widely depending upon specific reactants, the presence or absence of a solvent and the like. Any suitable set of reaction conditions known to the art may be used. Hydrocarbon solvents such as toluene or xylene are frequently used. Generally stoichiometric or equimolar ratios of reactants are used. However, more than molar or less than molar amounts may be used. In any event, reaction conditions are not viewed as critical.

The use of these quaternary ammonium salt derived thiadiazole reaction products and their subsequent hydrocarbyl anhydride derivatives provide exceptional antiwear and antioxidant activity with corrosion inhibiting and metal passivating properties.

The additives embodied herein are utilized in lubricating oil or grease compositions in an amount which imparts significant antiwear characteristics to the oil or grease as well as reducing the friction of engines operating with the oil in its crankcase. Concentrations of about 0.001 to about 10 wt. % based on the total weight of the composition can be used. Preferably, the concentration is from 0.1 to about 3 wt. %. It is expected that these materials would also be suitable for use in liquid hydrocarbyl or alcoholic or mixed hydrocarbyl/alcoholic or oxygenated fuel compositions. They are utilized in fuels in amounts of from about 25 to 500 pounds of additive per thousand barrels of fuel and preferably from about 50 to about 250 pounds per 1000 barrels of fuel.

The additives have the ability to improve the above noted characteristics of various oleaginous materials such as hydrocarbyl lubricating media which may comprise liquid oils in the form of either a mineral oil or a synthetic oil, or in the form of a grease in which the aforementioned oils are employed as a vehicle.

In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F. to about 6000 SSU at 100° F. and preferably, from about 50 to about 250 SSU at 210° F. These oils may have viscosity indexes ranging to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which is normally employed for thickening or gelling hydrocarbon fluids for foaming qrease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers. Ester-based lubricants are highly suitable.

The fuels contemplated are liquid hydrocarbon combustion fuels, including oxygenated and alcoholic fuels as well as distillate fuels and fuel oils.

It is to be understood, however, that the compositions contemplated herein can also contain other materials, for example, corrosion inhibitors, extreme pressure agents, low temperature properties modifiers and the like can be used as exemplified respectively by metallic phenates or sulfonates, sulfurized isobutylenes, acrylate polymers and the like. These materials do not detract from the value of the compositions of this invention, rather the materials serve to impart their customary properties to the particular compositions in which they are incorporated.

The following examples are merely illustrative and not meant to be limitations.

EXAMPLE 1

To a solution of 2-mercaptobenzothiazole (20 g, 0.12 mol) in methanol or isopropanol (100 ml) was added potassium hydroxide (6.7 g, 0.12 mol), followed by Aliquat 336 (tricaprylylmethylammonium chloride, Henkel Corp.) (48.3 g, 0.12 mol) (sodium hydroxide can also be used). The solid potassium chloride was filtered and the solvent was stripped to afford a dark brownish oil which was subsequently reacted with 2-dodecen-1-ylsuccinic anhydride (31.9 g, 0.12 mol) with or without toluene. The solvent was evaporated (if a solvent was used) to provide an antioxidant product as a dark brownish oil.

EXAMPLE 2

To a solution of 2,5-dimercapto-1,3,4-thiadiazole (30 g, 0.2 mol) in methanol or isopropanol (200 ml) was added potassium hydroxide (22.4 g, 0.4 mole) at ambient temperature (sodium hydroxide can also be used). The solution was stirred for 30 min. and Aliquat 336 (tricaprylylmethylammonium chloride, Henkel Corp.) (162 g, 0.4 mol) was slowly added. Potassium chloride precipitated out during the addition. When the addition was complete, the solution was continued stirring at ambient temperature for one hour. The mixture was filtered to remove the solid and the solvent was evaporated to afford a greenish oil which was used without purification. 2-Dodecen-1-ylsuccinic anhydride (106 g, 0.4 mol) was then added and further reacted with or without toluene as a solvent. The solution was filtered (if necessary) and the solvent was removed (if a solvent was used) to obtain the final product as a brownish oil which has a general structure as shown in FIG. 2.

EXAMPLE 3

To a solution of 2,5-dimercapto-1,3,4-thiadiazole (30 g, 0.2 mol) in methanol or isopropanol (200 ml) was added potassium hydroxide (22.4 g, 0.4 mol) at ambient temperature (sodium hydroxide can also be used). The solution was stirred for 30 min. and Aliquat 336 (tricaprylylmethylammonium chloride, Henkel Corp.) (162 g, 0.4 mol) was slowly added. Potassium chloride precipitated out during the addition. When the addition was complete, the solution was continued stirring at ambient temperature for one hour. The mixture was filtered and the solvent was evaporated to afford a greenish oil which was used without further purification. 2-Dodecen-1-ylsuccinic anhydride (53 g, 0.2 mol) was then added and further reacted with or without toluene as a solvent. The solution was filtered (if necessary) and the solvent was removed (if a solvent was used) to obtain the final product as a brownish oil which has a general structure as shown in FIG. 1.

EVALUATION OF PRODUCTS

The organic ammonium salt antioxidants thus obtained were blended into pentaerythritol derived ester lubricants and evaluated for antioxidant performance by the Catalytic Oxidation Test at 425° F. for 24 hours (Table 1). A comparison of the oxidation-inhibiting characteristics of the novel products with other commercially available hindered phenolic and arylamine antioxidants in the same base stocks was also conducted side by side; results are included.

CATALYTIC OXIDATION TEST

Basically, in the catalytic oxidation test, the lubricant is subjected to a stream of air which is bubbled through at the rate of five liters per hour at elevated temperatures for a specified time (Table 1, 425° F. for 24 hours). Present in the composition are samples of metals commonly used in engine construction, namely, iron, copper, aluminum, and lead. See U.S. Pat. No. 3,682,980, incorporated herein by reference for further details.

TABLE 1

Catalytic Oxidation Test (425° F., 24 hrs)

| Item | Additive Concentration (wt %) | Change in Acid Number Δ TAN | Change in Viscosity Δ KV (%) |
|---|---|---|---|
| Base oil (Pentaerythritol derived ester lubricant) | None | 8 | 210 |
| Commercial Arylamine Antioxidant (Ciba-Geigy Irganox L-57) in above oil | 1.0 | 3.5 | 38.2 |
| Commercial Phenolic Antioxidant (Ethyl Corp., Ethyl 702) in above oil | 1.0 | 5.0 | 96.9 |
| Example 1 in above oil | 1.0 | 1.6 | 24.8 |
| Example 2 in above oil | 1.0 | 1.5 | 27.6 |

TABLE 2

Four-Ball Wear Test 60 kg/2000 rpm/30 min/200° F.

| Item | Additive Concentration | Wear Scar (mm) |
|---|---|---|
| Base Oil (80% solvent paraffinic bright, and 20% solvent paraffinic neutral lubricant oils) | None | 3.48 |
| Example 1 in above oil | 1.0 | 1.5 |
| Example 2 in above oil | 1.0 | 0.70 |
| Example 3 in above oil | 1.0 | 2.01 |

It is clear from Table 1 that organic quaternary ammonium salt antioxidants prepared via FIGS. 1 and 2 exhibit excellent antioxidant activities as compared with commercially available arylamine and phenolic antioxidants in ester-based lubricants. This unprecedented class of compounds also displays good antiwear properties as evidenced by the data presented in Table 2. From these data, it can be concluded that the organic ammonium salt antioxidants described in FIGS. 2 and 3 are both good antioxidants and antiwear additives.

The organic quaternary ammonium salt antioxidants are an entirely new class of compounds which exhibit very good antioxidant and antiwear properties in ester-based lubricants under severe service conditions as exemplified by above test data. These properties can enhance the thermal and oxidative stability of premium quality automotive and industrial lubricants to extend their service life.

What is claimed is:

1. An improved lubricant composition comprising a major proportion of an oil of lubricating viscosity or grease prepared there from and a minor amount of from about 0.001 to about 10 wt % of a multifunctional antiwear, antioxidant additive product of reaction prepared by reacting a heterocyclic compound selected from the group consisting of mercaptothiadiazoles or dimercaptothiadiazole with a quaternary ammonium salt and a carboxylic acid anhydride in substantially molar, less than molar or more than molar amounts at temperatures varying from ambient to about 150° C. under pressures varying from ambient to slightly higher for a time sufficient to obtain the desired additive product of reaction.

2. The composition of claim 1 wherein the product contains the following structural formula:

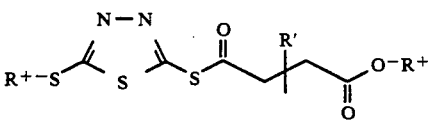

(Figure 2)

and wherein $R^+$ is $N+R_1R_2R_3R_4$, a tetra-substituted ammonium ion in which the groups attached to the nitrogen may be the same or different and $C_1$ to about $C_{40}$ hydrocarbyl optionally containing sulfur, oxygen, nitrogen or mixtures thereof and $R'$ is $C_1$ to about $C_{40}$ hydrocarbyl or polyhydrocarbyl selected from the group consisting of alkyl, aryl, alkaryl or aralkyl.

3. The composition of claim 1 wherein the product contains the following structural formula:

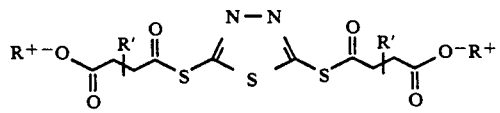

and wherein $R^+$ is $N+R_1R_2R_3R_4$, a tetra-substituted ammonium ion in which the groups attached to the nitrogen may be the same or different and $C_1$ to about $C_{40}$ hydrocarbyl optionally containing sulfur, oxygen, nitrogen or mixtures thereof and $R'$ is $C_1$ to about $C_{40}$ hydrocarbyl or polyhydrocarbyl selected from the group consisting of alkyl, aryl, alkaryl or aralkyl.

4. The composition of claim 1 wherein the heterocyclic compound is a dimercaptothiadiazole.

5. The composition of claim 4 wherein the heterocyclic compound is 2,5-dimercapto-1,3,4-thiadiazole.

6. The composition of claim 1 wherein the reactants are 2,5-dimercapto-1,3,4-thiadiazole, tricaprylmethylammonium chloride, and 2-dodecen-1-ylsuccinic anhydride.

7. The composition of claim 1 wherein the lubricant is an oil of lubricating viscosity selected from the group consisting of (1) mineral oils, (2) synthetic oils, (3) or mixtures of mineral and synthetic oils or is (4) a grease prepared from any one of (1), (2) or (3).

8. The composition of claim 7 wherein the lubricant contains from about 0.001 to about 10 wt% based on the total weight of the composition of the additive product of reaction.

9. The composition of claim 7 wherein the lubricant is a synthetic oil.

10. The composition of claim 9 wherein the lubricant is an ester oil.

11. A process for preparing a multifunctional antioxidant, antiwear additive product by reacting a heterocyclic compound selected from the group consisting of mercaptothiadiazoles or dimercaptothiadiazoles with a quaternary ammonium salt and a hydrocarbyl carboxylic acid with anhydride in substantially molar, less than molar or more than molar ratios at temperatures varying from ambient to about 150° C. under pressures varying from ambient to slightly higher for a time sufficient to obtain the desired additive product of reaction.

12. The process of claim 11 wherein the product contains the following structural formula:

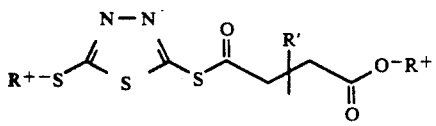

and R+ is N+R₁R₂R₃R₄, a tetra-substituted ammonium ion in which the groups attached to the nitrogen may be the same or different and are $C_1$ to about $C_{40}$ hydrocarbyl optionally containing sulfur, oxygen, nitrogen or mixtures thereof and R' is $C_1$ to about $C_{40}$ hydrocarbyl or polyhydrocarbyl selected from the group consisting of alkyl, aryl, alkaryl or aralkyl.

13. The process of claim 11 wherein the product contains the following structural formula:

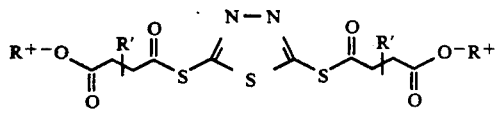

and wherein R+ is N+R₁R₂R₃R₄, a tetra-substituted ammonium ion in which the groups attached to the nitrogen may be the same or different and are $C_1$ to about $C_{40}$ hydrocarbyl optionally containing sulfur, oxygen, nitrogen or mixtures thereof and R' is $C_1$ to about $C_{40}$ hydrocarbyl or polyhydrocarbyl selected from the group consisting of alkyl, aryl, alkaryl or aralkyl.

14. The process of claim 11 wherein the heterocyclic compound is a dimercaptothiadiazole.

15. The process of claim 14 wherein the heterocyclic compound is 2,5-dimercapto-1,3,4-thiadiazole.

16. The process of claim 11 wherein the reactants are 2,5-dimercapto-1,3,4-thiadiazole, tricaprylmethylammonium chloride, and 2-dodecen-1-ylsuccinic anhydride.

17. A product of reaction suitable for use as an antioxidant and antiwear additive in lubricants prepared by reacting a heterocyclic compound selected from the group consisting of mercaptothiadiazoles or dimercaptothiadiazoles with a quaternary ammonium salt and carboxylic acid anhydride in substantially molar, less than molar or more than molar amounts at temperatures varying from ambient to about 150° C. under pressures varying from ambient to slightly higher for a time sufficient to obtain the desired additive product of reaction.

18. The product of claim 17 wherein the product contains the following structural formula:

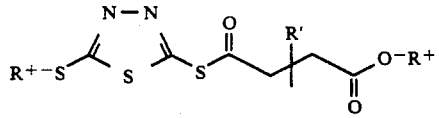

and wherein R+ is N+R₁R₂R₃R₄, a tetra-substituted ammonium ion in which the group attached to the nitrogen may be the same or different and is $C_1$ to about $C_{40}$ hydrocarbyl optionally containing sulfur, oxygen, nitrogen or mixtures thereof and R' is $C_1$ to about $C_{40}$ hydrocarbyl or polyhydrocarbyl selected from the group consisting of alkyl, aryl, alkaryl or aralkyl.

19. The product of claim 17 wherein the product contains the following structural formula:

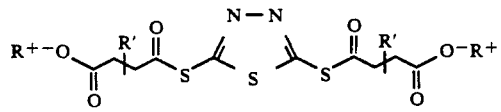

wherein R+ is N+R₁R₂R₃R₄, a tetra-substituted ammonium ion in which the groups attached to the nitrogen may be the same or different and are $C_1$ to about $C_{40}$ hydrocarbyl optionally containing sulfur, oxygen, nitrogen or mixtures thereof and R' is $C_1$ to about $C_{40}$ hydrocarbyl or polyhydrocarbyl selected from the group consisting of alkyl, aryl, alkaryl or aralkyl.

20. The product of claim 17 wherein the heterocyclic compound is a dimercaptothiadiazole.

21. The product of claim 20 wherein the heterocyclic compound is 2,5-dimercapto-1,3,4-thiadiazole.

22. The product of claim 17 wherein the reactants are 2,5-dimercapto-1,3,4-thiadiazole, tricaprylmethylammonium chloride, and 2-dodecen-1-ylsuccinic anhydride.

23. A method of preparing an improved lubricant composition comprising adding to said lubricant a minor multifunctional antioxidant, antiwear amount of an additive product of reaction as described in claim 17.

* * * * *